United States Patent [19]

Lau

[11] Patent Number: 5,171,754

[45] Date of Patent: Dec. 15, 1992

[54] USE OF OXIDIZED POLYAMINES, ESPECIALLY NN'-BIS-(3-PROPIONALDEHYDE)-1-4-DIAMINOBUTANE (SPERMINE DIALDEHYDE) AS IMMUNOSUPPRESSIVE AGENTS

[75] Inventor: Catherine Y. Lau, Unionville, Canada

[73] Assignee: Ortho Pharmaceutical Corporation, Raritan, N.J.

[21] Appl. No.: 586,326

[22] Filed: Sep. 18, 1990

Related U.S. Application Data

[63] Continuation of Ser. No. 262,760, Oct. 26, 1988, abandoned.

[51] Int. Cl.$^5$ .............................................. A61K 31/13
[52] U.S. Cl. ................................................ 514/666
[58] Field of Search ..................................... 514/666

[56] References Cited

PUBLICATIONS

Alarcon et al., Archives of Biochemistry and Biophysics 94 (1961).
Tabor, Celia and Sanford and Rosenthale, "Pharmacology of Spermine and Spermidine—Some Effects on Animals and Bacteria" Aug. 1955.
Tabor et al, "Identification of the Aminoaldehydes Produced by the Oxidation of Spermine and Spermidine with Purified Plasma Amine Oxidase", Journal of Biological Chemistry, vol. 239, 2194-2203 (1964).
Fukami et al., Biochemical and Biophysical Research Communications, vol. 28, No. 1, (1967): "Phagocidal Action of Oxidized Spermine and Its Analogues".
K. Kremzner, Leon and Donald H. Harter, Biochemical Pharmacology, vol. 19, pp. 2541-2550, (1969), "Antiviral Activity of Oxidized Polyamines and Aldehydes".
Bachrach, U., and F. Don, Journal of General Virology, vol. 11, (1) 1-9,: (1971): "Inactivation of Myxoviruses by Oxidized Polymines".
Kimes, Brian and David R. Morris, Biochimica et Biophysica Acta, vol. 228 (1971), pp. 223-234 (1970): "Preparation and Stability of Oxidized Polymines".
Bachrach, U. and E. Rosenkovitch, Applied Microbiology, vol. 23, No. 2, (1972) pp. 232-235: "Effective Oxidized Spermine and Other Aldehydes on the Infectivity of Vaccina Virus".
Nishimura, et al., Agricultural Biological Chemistry, vol. 39 (A) 1663-1666 (1975): "Phagocidal Activity of the Hydrolyzate of Acetal Derivatives of Oxidized Spermine and its N, N'Dimethyl Analogue".
Byrd et al., Nature vol. 267, (1977) pp. 621-623: "Synthetic Polyamines Added to Cultures Containing Bovine Sera Reversibly Inhibit In Vitro Parameters of Immunity".
Allen et al., Nature Volume 267 (1967) pp. 623-625: "Identification of a Thymic Inhibitor (Chalone) of Lymphocyte Transformation as A Spermine Complex".
Byrd et al., Advances in Polyamine Research, vol. 2, (1978) pp. 71-83: "Influence of Synthetic Polyamines on In Vitro Responses of Immunocompetent Cells".
Joseph M. Gaugas, Polyamines in Biomedical Research (1980) J. M. Gaugas, Editor John Wiley & Sons: "Biogenic Diamines and Polyamines in Support and in Inhibition of Lymphocyte Proliferation".
Bachrach et al., Advances in Polyamine Research vol. 3, Edited by C. M. Caldarera et al., Raven Press, N.Y., 1981: "Polyamine Biosynthesis and Metabolishm in Transformed Human Lymphocytes".

(List continued on next page.)

Primary Examiner—Frederick E. Waddell
Assistant Examiner—Zohreh A. Fay
Attorney, Agent, or Firm—Gale F. Matthews

[57] ABSTRACT

This invention relates to the use of oxidized polyamines, and especially aminoaldehydes such as spermine bisaldehyde both in vitro and in vivo to elicit an immunosuppressive response in living cells. It also relates to the therapeutic application of these compounds to induce an immunosuppressive response in living organism.

25 Claims, 7 Drawing Sheets

OTHER PUBLICATIONS

Abbott, A. C. and C. C. Bird, vol. 115, No. 2, (1983), pp. 727-742, Biochemical and Biophysical Research Communications: "Cyytolethal Sensitivity of Human Lymphoid Cells to Glucocorticoids and Oxidized Polyamines".

Labib, R. and Thomas B. Tomasi, European Journal of Immunology vol. 11, pp. 266-269 (1981): "Enzymatic Oxidation of Polyamines, Relationship to Immunosuppressive Properties".

Frolik, et al., Archives of Biochemistry and Biophysics, vol. 230, No. 1, Apr., pp. 93-102 (1984): "Inhibition of Transforming Growth Factor-Induced Cell Growth and Soft Agar by Oxidized Polyamines".

Smith, et al., Biochemical Society Transactions, pp. 326-329, vol. 13; "Inhibition of Cell Proliferation by Polyamines Does Not Depend on the Cytotoxicity of Acrolein" (1985).

A. Ferrante, Immunology, vol. 54, pp. 785-789 (1985): "Inhibition of Human Neutrophil Locomotion by the Polyamine Oxidase-Polyamine System".

Israel et al., vol. 16, No. 1, (1973): "Synthesis and Anti--Tumor Evaluation of the Presumed Cytotoxic Metabolytes of Spermine and N,N'-bis (3-amino propyl) Nonane-1,9-diamene".

GB Patent Application GB 2017492: (Oct. 1979).

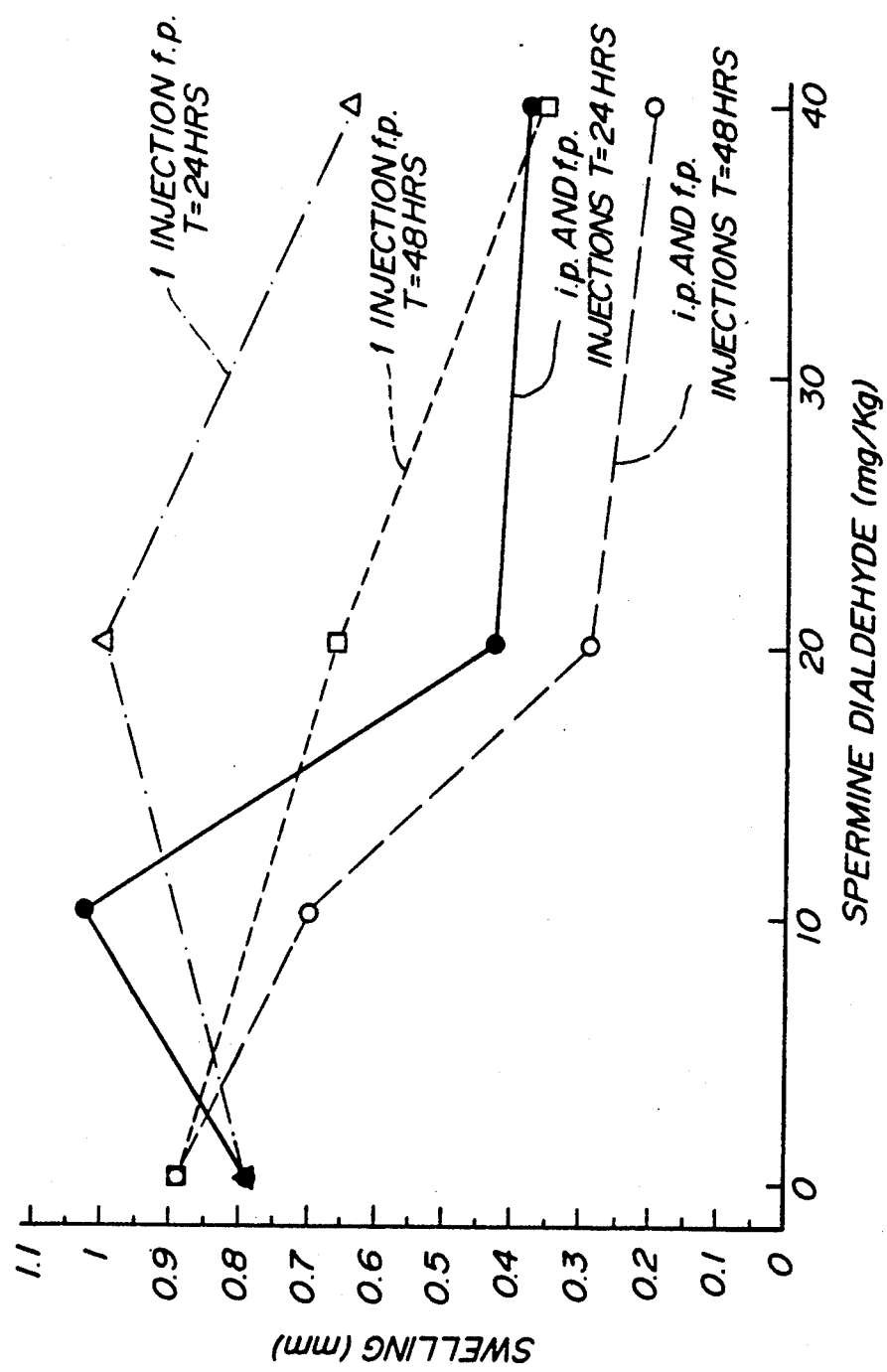

USE OF OXIDIZED POLYAMINES, ESPECIALLY NN'-BIS-(3-PROPIONALDEHYDE)-1-4-DIAMINOBUTANE (SPERMINE DIALDEHYDE) AS IMMUNOSUPPRESSIVE AGENTS

This is a continuation of application Ser. No. 262,760, filed Oct. 26, 1988, now abandoned.

BACKGROUND

This invention relates to the use of oxidized polyamines, and especially aminoaldehydes such as NN'-Bis-(3-propionaldehyde)-1-4-diaminobutane (spermine bisaldehyde) both in vitro and in vivo to elicit an immunosuppressive response in living cells. It also relates to the therapeutic application of these compounds to induce an immunosuppressive response in a living organism.

DESCRIPTION OF THE ART

Polyamines such as spermine, spermidine and putrescine are widely distributed in mammalian cells, although they are found to differ in their relative concentrations. Oxidized polyamines are believed to inhibit growth of parasites (D. M. L. MORGAN and J. R. CHRISTENSEN, Adv. Polyamine Res., 4, 169-174 (1983); D. M. L. MORGAN, U. BACHRACH, Y. G. ASSARAF, E. HARARI and J. GOLENSER, Biochem. J., 236, 97-101 (1986)), suppress infectivity of selected strains of phage and bacteria (U. BACHRACH, S. DON and H. WIENER, J. Gen. Virol., 13(Pt. 3), 415-22 (1971); K. NISHIMURA, T. KOMANO and H. YAMADA, Biochim. Biophys. Acta, 247(1), 153-6 (1971) J. G. HIRSCH and R. J. DUBOS, J. Exp. Med., 95, 919 (1952); C. W. TABOR and S. M. ROSENTHAL, J. Pharmacol., 116, 139 (1956)) and inactivate several strains of viruses (U. BACHRACH and E. ROSENKOVITCH, Appl. Microbiol., 23(2), 232-5 (1972); U. BACHRACH and S. DON, J. Gen. Virol., 11(Pt. 1), 1-9 (1971); U. BACHRACH, C. W. TABOR and H. TABOR, Biochem. Biophys. Acta, 78, 768 (1963); U. BACHRACH and J. LEIBOVICI, Isr. J. Med. Sci., 1, 541 (1965); J. SCHINDLER, Experientia, 21, 697 (1965); E. KATZ, T. GOLDBLUM, U. BACHRACH and N. GOLDBLUM, Isr. J. Med. Sci., 3, 575 (1967)). The literature does not make clear however, whether the inhibitory effect is due to aminoaldehydes or other toxic side products such as hydrogen peroxide and ammonia released during the oxidation of spermine by PAO.

Hence, despite the impressive list of studies performed with oxidized spermine, the actual molecular structure(s) mediating the specific immunosuppressive or inhibitory activities is unknown. Oxidation of spermine by PAO revealed six major oxidation products in addition to ammonia and hydrogen peroxide (R. S. LABIB and T. B. TOMASI, JR., Eur. J. Immunol., 11, 266-269 (1981)). The inhibitory effect of each of the products has not been analyzed but it was believed that the dioxidized spermine or spermine dialdehyde (NN'-Bis-(3-propionaldehyde)-1-4-diaminobutane) would demonstrate activity. Israel et al, Supra, synthesized this molecule together with another analogue and found that both compounds exhibited cell inhibitory activities in vitro. These investigations however failed to find significant in vivo efficacy with the dialdehydes they synthesized. Furthermore, these molecules were quite toxic, spermine dialdehyde (NN'-Bis-(3-propionaldehyde)-1-4-diaminobutane) showed severe acute toxicity with an $LD_{100}$ at 40 mg/kg when given intraperitoneally.

BRIEF DESCRIPTION OF THE DRAWINGS

FIG. 7 illustrates the suppression of delayed type hypersensitivity by spermine dialdehyde. Delayed type hydersensitivity was induced in the footpad of B6D2F1 mice and swelling measured in mm. Spermine dialdehyde was administered i.p. and i.m. at various time periods. The graph plots swelling (mm) vs. spermine dialdehyde (mg/kg). One injection in the footpad at 24 hours is indicated on the graph by a broken line interrupted by a clear triangle. One injection at 48 hours is indicated by a broken line interrupted by a clear square. I.p. and f.p. injections at 24 hours are indicated by a broken line interrupted by black circles; and i.p. and f.p. injections at 48 hours are indicated by a broken line interrupted by clear circles.

SUMMARY OF THE INVENTION

Figure 1:
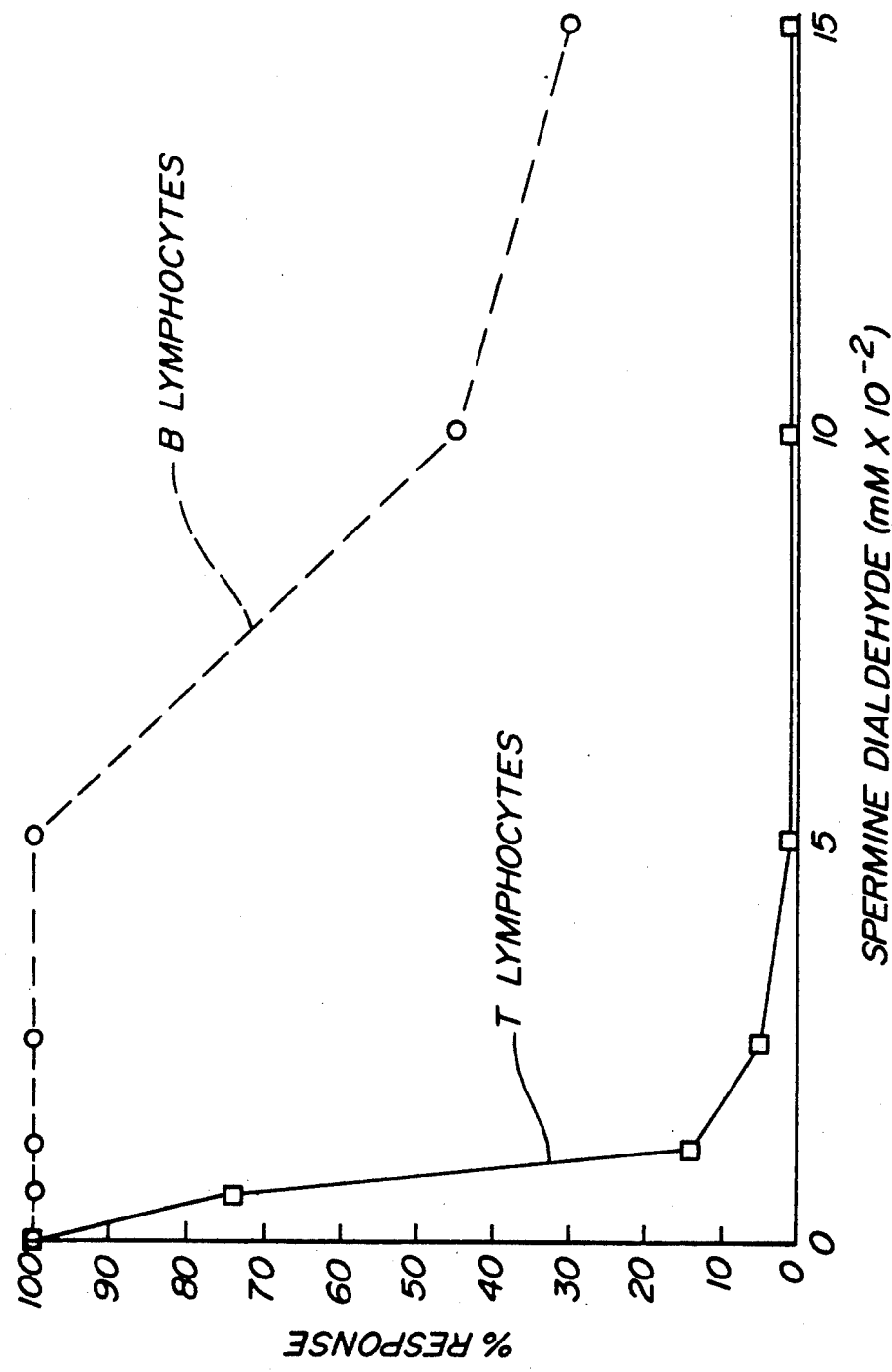
FIG. 1 depicts in vitro suppression of human B lymphocytes and T lymphocytes by spermine dialdehyde. Human T & B lymphocytes were incubated separately with different concentrations of spermine dialdehyde in vitro for 1 hour. Cells were washed extensively and set up in a PHA (for T cell) or PWM (B cell) proliferation assay. A graph is depicted wherein percentage of response (T cell indicated by square; B cell indicated by circle) is plotted as a function of concentration of spermine dialdehyde ($10^{-2}$ mM).

The present invention provides a method for inducing an immunosuppressive response in living cells which effective amount of a substantially pure form of a compound having the General Formula:

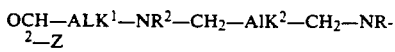

wherein
$ALK^1$ is independently alkylene;
$R^2$ is independently hydrogen or $-CH_2R^3$;
$R^3$ is independently alkyl;
$ALK^2$ is alkylene;
Z is H or $ALK^1-CHO$;
or the acid addition salt thereof.

General Formula I

This immunosuppressive response is particularly selective for the suppression of the proliferation of T cell populations, especially the helper T cell and cytotoxic T cell subpopulations.

Also provided are methods for inducing an immunosuppressive response in a living organism which comprises the administration of a compound having the above formula to said organism, in substantially pure form and in an amount effective to induce said response.

The methods as described herein are particularly suitable in the therapeutic control of various immunologically related disease states such as graft vs. host rejections, delayed hypersensitivity and the like.

DETAILED DESCRIPTION OF THE INVENTION

The present inventors have discovered that compounds, particularly those obtained by synthetic methods, having the General Formula:

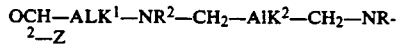

wherein
$ALK^1$ is independently alkylene;
$R^2$ is independently hydrogen or $-CH_2R^3$;
$R^3$ is independently alkyl;
$ALK^2$ is alkylene;
Z is H or $ALK^1-CHO$;
or the acid addition salt thereof.

General Formula I are useful in inducing an immunosuppressive response in living cells when applied to those cells in substantially pure form. Particularly useful are compounds of General Formula I wherein $ALK^1$ $ALK^2$, and $R^3$ are each independently straight or branched chain alkylene of about 1 to about 8 carbons, preferably about 1 to about 6 carbons, more preferably about 1 to 4 carbon atoms, and most preferably about 1 to about 2 carbon atoms. In more preferred embodiments, $R^2$ is hydrogen. In the particularly preferred embodiments, Z is $ALK^1-CHO_1$, $R^2$ is hydrogen, and $ALK^1$ and $ALK^2$ are each independently about 1 to about 6 carbon atoms, preferably about 1 to about 4 carbon atoms, most preferably about 1 to about 2 carbon atoms. Of the most preferred compounds for use herein may be mentioned spermine dialdehyde.

The presently described compounds are also useful in the therapeutic inducement of an immunosuppressive response in a living organism. In particular, one of the compounds, synthetic spermine dialdehyde, used according to the present invention has demonstrated enhanced efficacy and a substantially reduced toxicity [not lethal up to 400 mg/kg, contrary to what was reported in the literature ($LD_{100}$ 40 mg/kg, Israel (1973) Supra)]. The use of these molecules, particularly spermine dialdehyde, both in in vitro applications as well as in vivo applications to induce an immunosuppressive response is therefore described in detail herein.

As used herein, the term "immunosuppressive response" refers to a suppression in the proliferation of cell types originating from hemopoietic stem cells, particularly the lymphoid lineage. The use of the compounds as described herein is particularly suitable in the selective suppression of the T-cell population, particularly the T-cytotoxic, T-helper subpopulations. The immunosuppression may also be described as antigen nonspecific, which is exemplified by a 99% suppression of mitogen-induced T cell proliferation. In some cases, contrary to the art, this selective suppression has been shown to be irreversible.

The compounds for use as described herein may be obtained in any convenient manner. The compounds are preferably used in "substantially pure form" which means substantially free of enzymes or other agents that might be present during their formation, and that will interfere with its efficacy or that might increase toxicity. Hence, in their preferred form, the compounds are preferably 95% pure, more preferably 99% pure, and most preferably 100%, as measured by nuclear magnetic resonance, mass spectro analysis, and HPLC. Inert materials may be present in trace amounts.

The compounds may be obtained by enzymatic oxidation of naturally occurring polyamines by techniques known to the art, as long as the product is purified from the enzymes using conventional purification means such as chromatography and the like. Suitable enzymes for use in an enzymatic oxidation process are those effective to bring about the rapid oxidative deamination of the natural polyamine. Illustrative of such enzymes are amine oxidases obtained from ruminant sera such as beef serum, sheep serum, fetal calf serum and the like. Also applicable are oxidases obtained from mouse amniotic fluid, human pregnant sera, and the like.

To avoid interference with contaminants, it is preferred that the compound be synthesized de novo, using organic synthesis techniques such as those described below. In the particularly preferred embodiments, compounds for use herein are amino dialdehydes. The dialdehyde compound is synthesized by conversion of a diacetal in the presence of an acid. Preferred diacetals are represented by Formula:

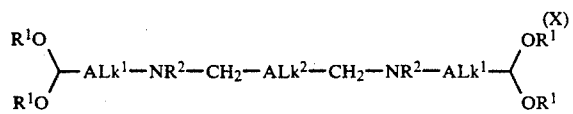

wherein
- $R^1$ is independently alkyl or benzyl
- $ALk^1$ is independently alkylene;
- $R^2$ is independently hydrogen or —$CH_2R^3$
- $R^3$ is independently alkyl; and
- $ALk^2$ is alkylene, Preferred reactions may be exemplified by the following schemes:

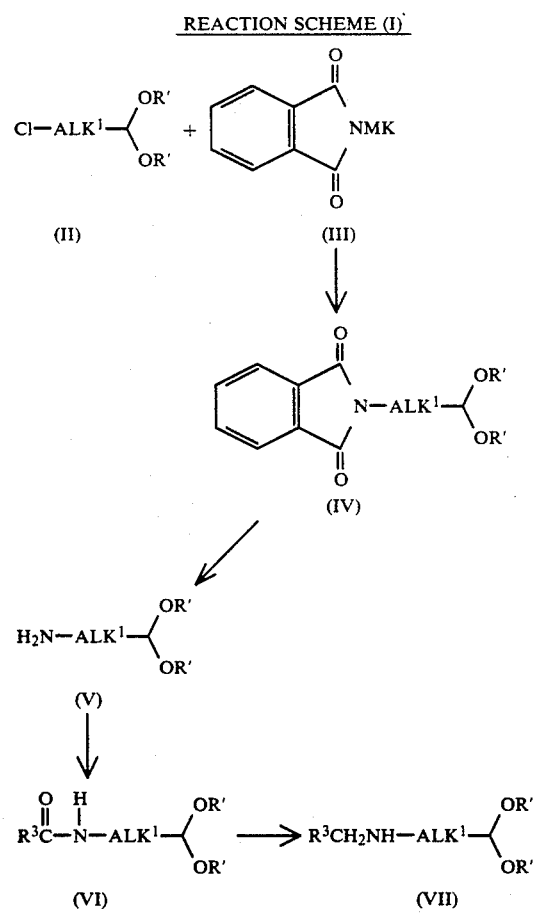

REACTION SCHEME (II)

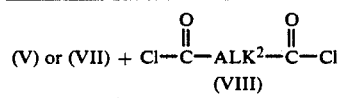

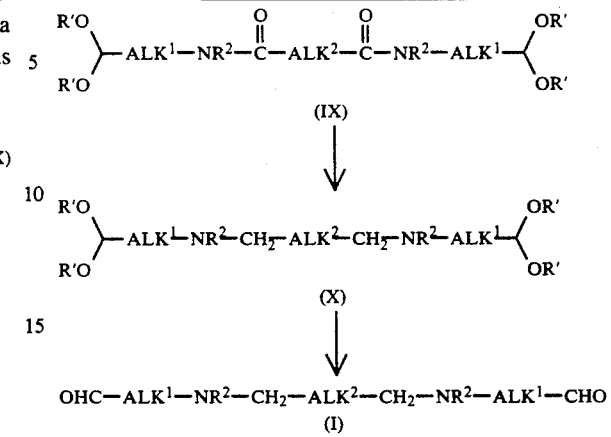

The above reaction Schemes I and II set forth a summary of preferred syntheses for compounds of Formula (X) which may be stored and used to generate compounds of General Formula (I).

A chloroaldehyde of Formula (II) in acetal form is reacted with potassium phthalimide of Formula (III) in equal molar amounts at an elevated temperature to yield the phthalimide of Formula (IV). Examples of the compound of Formula (II) are 3-chloroacetaldehyde diethyl acetal and 3-chloro propionaldehyde diethylacetal. The amine is then released by reaction with hydrazine at an elevated temperature, yielding the primary amine of Formula (V). The primary amine (V) can then be taken on as shown in Reaction Scheme II or can be modified to produce a secondary amine. For the secondary amine, the primary amine of Formula (V) is reacted with an anhydride such as formic-acetic anhydride or acetic anhydride at temperatures that can vary from about 0° C. to about room temperatures to yield the amide of Formula (VI). The amide is then reduced with lithium aluminum hydride in tetrahydrofuran at reflux to yield the secondary amine of Formula (VII). In Formulae (II), (IV), (V), (VI), and (VII), $R^1$, $ALK^1$ and $R^3$ are as defined for Formula (X) above.

To prepare the dibenzyl acetal of Formula (V) or (VII) the corresponding diethyl compound may be dissolved in a solvent and reacted with benzyl alcohol in the presence of a small amount of acid such as trichloracetic acid followed by distillation to drive off the ethanol byproduct. For a different alkyl moiety, the diethyl compound may be dissolved in the alcohol, e.g. methanol for the dimethyl acetal, and reacted as in the benzyl case. To avoid cyclization, it may be preferable to subject a compound of Formula II to this treatment, due to the presence of the acid.

In Reaction Scheme II, the primary or secondary amine, designated as compound (V) or (VII), respectively, is reacted with a diacid chloride of Formula (VIII). Examples of diacid chlorides are succinyl chloride and glutaryl chloride. The reaction is conducted at a low temperature of about −70° to −20° in the presence of a mild base such as triethylamine to yield the diamide of Formula (IX). The diamide (IX) is then reduced with a reducing agent such as lithium aluminum hydride in tetrahydrofuran at reflux to yield the diamine diacetal of Formula (X). The diamine diacetal (X) can be stored for extended periods and brought to the site of administration to a patient for the conditions described above. After reduction with lithium aluminum hydride, the final product is preferably purified by making the crystalline salt form of the diamine (X) with an acid. The free amine can then be resynthesized from the salt. However, storage may be easier with the salt form. It should be noted that creation of the salt with acid must be carried out carefully since excessive amounts of the acid will destroy the acetal moieties.

For release of a dialdehyde of General Formula (I), the diacetal (X) would be reacted with an acid such as hydrochloric acid to yield the free dialdehyde. Sodium hydroxide may be used to regenerate (X) from the salt form, if desired.

For a compound of Formula (IX), and thus of (X) and (I), where the two $ALK^1$ moieties are not the same, a single mole of the amine (V) or (VII) is reacted with the anhydride corresponding to the diacid chloride of formula (VIII), e.g. succinic anhydride. The thus-produced mixed carboxylic acid-amide is then reacted with a mole of a different amine of formula (V) or (VII) using a peptide coupling reagent such as (2-ethoxy-1-ethoxycarbonyl-1,2-diahydroquinoline, known as EEDQ, or 1,3-dicyclohexylcarbodiimide, known as DCC, to yield an amide of formula (IX) wherein the two $ALK^1$ moieties are not the same.

One skilled in the art will understand that concentrations of oxidized polyamines suitable for use herein are concentrations effective to induce the desired immunosuppressive response without exhibiting substantial cell toxicity. Effective concentrations may vary widely according to the particular cells it is desired to immunosuppress, and the organism from which these cells are obtained. Exemplary concentrations for use herein may be extrapolated from the preferred concentrations for spermine dialdehyde. These concentrations generally range from about 0.01 mM to about 0.2 mM, more preferably about 0.03 mM to about 0.1 mM, and most preferably about 0.03 mM to about 0.06 mM.

The immunosuppressive response induced by the techniques described herein, and the efficacy of the dosing, may also be measured in vitro by methods conventional to the art. This may be accomplished by the incubation of cells to be immunosuppressed with various concentrations of the compound, and comparison of the ensuing proliferation of these cell populations with that of control samples that have not been treated with the , compound as described herein.

The oxidized polyamines are administered to the cells in any suitable physiologically compatible vehicle such as saline, phosphate buffer saline, methycellulose solutions, and the like. Solutions of the compound or homogeneous ions are preferred for such administration. The cells are allowed to incubate with the compound in a suitable growth medium such as minimum essential medium (MEM), RPMI 1640 and other suitable tissue culture media, to maintain cellular viability. This incubation generally takes place for a period of time sufficient to induce suppression of cell proliferation of at least about 25%, and preferably at least about 50%, as compared to control values of cellular growth. The incubation generally ranges for a period of time of about 10 minutes to about 1 hour, preferably about 10 minutes to about 30 minutes.

Representative of the therapeutic use of cells treated with oxidized polyamines, is the treatment of bone marrow extracts ex vivo with spermine dialdehyde prior to transplantation of these extracts into a patient. Treatment with the spermine dialdehyde can inactivate T lymphocytes without exhibiting toxic effects on the marrow cells themselves. This phenomenum has been shown to alleviate typical graft vs. host reactions, which are noted as being lethal to patients undergoing bone marrow transplantations. Suitable treatment parameters for such bone marrow extracts in human subjects may be the ex vivo treatment of cells as described above.

The present inventors have also discovered that direct in vivo administration of the compounds may also be effective to elicit an immunosuppressive response in an organism. For example, it has been discovered that in vivo administration of the compound spermine dialdehyde can greatly reduce graft vs. host reactions in a living organism. It has further been discovered that administration of this compound will suppress the generation of cytotoxic T cells. It is believed that cytotoxic T cells play a role in the mediation of organ graft rejections, and thus, in vivo suppression of these cells will lead to prolonged graft survival. Hence, it should be appreciated that the in vivo administration of these compounds has far-reaching therapeutic advantages.

Skin graft prolongation has been used by immunologists to predict the efficacy of compounds in suppressing organ rejection. For instance, anti-Thy 1 antibody (mouse equivalent of Orthoclone OKT3) (R. M. Gorcyzynski, M. Boulanger and C. Lau. J. Immunol. 138:3197-3202 (1987)), FN18 (Frans J. M. Nooij and Margreet Jonker, "The effect on skin allograft survival of a monoclonal antibody specific for a polymorphic CD3-like cell surface molecule in rhesus monkeys". Eur. J. Immunol. 1987. 17:1089-1093), (monkey equivalent of Orthoclone OKT3) were all effective in suppressing skin graft rejection and Orthoclone OKT3 turned out to be effective in suppressing solid organ rejection in humans (Cosimi, A. B., Burton, R. T., Colvin, R. B., Goldstein, G., Delmonico, F. L., Laguaglia, M. P. Tolkoff-Rubin, N., Rubin, R. H., Herrin, J. T., and Russell, P. S., Transplantation 1981. 32:535). CsA, a potent immunosuppressive molecule for organ transplantation is also effective in skin graft experiments. Taken together, the data reported below suggest that spermine dialdehyde, which is more effective than a comparable dose of CsA, should be at least as active as CsA in stopping organ rejection after transplantation.

Hypersensitivity is involved with allergic reactions (DeWeck, A. 1983. Regulation of IgE responses, New Trends in Allergy, J. Ring and G. Burg (eds.). Springer-Verlag, Berlin) and autoimmunity (allergic encephalomyelitis) (Weigle, W. O. 1980, Analysis of autoimmunity through experimental models of thyroiditis and allergic encephalomyelitis, Adv. Immunol. 30, 159). The fact that spermine dialdehyde suppressed DTH suggests that it might be useful in certain forms of autoimmunity. One injection of spermine dialdehyde in the footpad suppressed swelling and inflammation, suggesting that it can be used for treatment of inflamed joints in Rheumatoid Arthritis (RA) patients through direct injection into the joint. For RA patients experiencing acute flare of the disease, direct injection into the joint with prednisone is a very common treatment. Spermine dialdehyde could supplement or substitute for prednisone in the treatment of inflamed joints in RA patients.

Compounds administered therapeutically according to the method of the invention may be prepared as described above, and are also preferably dialdehydes synthesized from a diacetal. Formulations containing the oxidized polyamines or pharmaceutically acceptable salts thereof may also be used in this method, including ingredients such as conventional pharmaceutically acceptable carriers, like saline or sterile water, or ingredients to aid solubility or preservation of the formulation.

The preferred in vivo mode of administration of the compounds according to the method of this invention to achieve the desired immunosuppression is parenteral, more preferably intravenous or subcutaneous, and most preferably subcutaneous. It is not believed, however, that the specific mode of administration is critical to the practice of the present method so long as an effective amount of the compound enters the blood stream.

In certain embodiments, the present inventors have found that about 5-10 mg/kg of spermine dialdehyde administered intraveneously or subcutaneously was effective to suppress graft vs. host reactions, as detailed in the Examples section. However, it is believed to be well within the skill of a practitioner in the field to determine other appropriate doses of compounds and frequencies of administration to achieve the desired immunosuppressive response. Subcutaneous dosing of about 10 mg/kg i.p.-20 mg/kg i.p. correlated well with the i.v. dosing. It is contemplated that for subcutaneous administration, those skilled in the art would recognize the necessity to increase the dose. Accordingly, the only practical limits are dictated by optimum efficacy, and hence, all such doses, frequencies of administration, and modes of administration are intended to be included within the subject method.

Efficacy of the method of the invention may be determined by observations of the clinical manifestations of graft vs. host reactions (either in the human or in one or more animal species) such as hunched back, diarrhea, alopecia, poor physical condition, wasting, and in the most drastic cases, death. Reduction of these symptoms would be an indication that the compound is exerting its effect, at the chosen dosage. Signs of toxicity, for example, leukopenia, anemia, lack of reconstitution, and the like would indicate that the dosage should be reduced.

Indirect measurement of efficacy may also be useful in establishing and monitoring dosage levels. For example, this may be determined by assaying the cytotoxic T cell populations by mixed lymphocyte reaction assays, using peripheral T cells.

The following examples more specifically describe certain embodiments of the present invention but should not be considered limitative thereof.

EXAMPLES

I. Chemical Synthesis of N'N'-Bis(3,3-diethoxypropyl)-1,4 butanediamine nitrate spermine (bis-acetal)

All materials were obtained from Aldrich. All reactions are run under an atmosphere of nitrogen, and solvents are either HPLC grade (methanol, methylene chloride, NMP, ethyl acetate) or anhydrous "Gold Label" grade (THF).

1. Preparation of N-(3,3-diethoxypropyl)phthalimide (Compound 1), A mixture of 3-chloropropionaldehyde diethyl acetal (16.7 g, 0.10 mol) and potassium phthalimide (18.5 g, 0.10 mol) in N-methylpyrrolidinone (200 ml) was stirred overnight at 125° C. under nitrogen. The resulting solution was cooled and poured into water (400 ml) and the resulting mixture was extracted with ether (2×200 ml). The ether extracts were washed with water (2×100 ml), dried (MgSO₄), filtered, and evaporated to leave an orange oil. Chromatography on silica (200 g) with 95:5 methylene chloride-ether provided pure Compound 1 as a pale orange oil (16.5 g, 60%).

2. Preparation of 3,3-diethoxypropylamine (Compound 2), A solution of N-(3,3-diethoxypropyl)phthalimide (1) (16.5 g, 59.5 mmol) and hydrazine (3.8 g, 120 mmol) in methanol (300 ml) was stirred at reflux for 4 hours (a mechanical stirrer was necessary as the mixture thickened considerably). The mixture was cooled with continued stirring, and filtered, washing the precipitate with methanol. The filtrate was evaporated to a semi-solid mass, which was taken up in methylene chloride (150 ml) and filtered again. The filtrate was concentrated and the residue was distilled in vacuo to provide Compound 2 as a colorless liquid (6.5 g, 70%). (The reported boiling point is ca. 60° C. at 4 mm of Hg, ca. 70° C. at 20 mm of Hg.).

3. Preparation of N,N'-bis(3,3-diethoxypropyl)succinamide (Compound 3), A solution of succinyl chloride (3.25 g, 21.0 mmol) in methylene chloride (50 ml) is added dropwise with vigorous stirring to a cold (−50° C.) solution of Compound 2 (6.14 g, 41.7 mmol) and triethylamine (6.3 ml, 45 mmol) in methylene chloride (200 ml). The mixture was allowed to warm to room temperature and stirred under nitrogen overnight. The solvent was evaporated and the residue was taken up in ether (200 ml). The resulting suspension was filtered, and the filtrate evaporated. The residue was chromatographed on silica (150 g) with 6:1 from hexane to provide 3 as a colorless solid, mp 89-90° C. (4.2 g, 53%). The material decomposed over a period of two months when stored at room temperature.

4. Preparation of N,N'-bis(3,3-diethoxypropyl)butane-1, 4-diamine dinitrate (Compound 4), A mixture of Compound 3 (4.0 g, 10.6 mmol) and lithium aluminum hydride (0.84 g, 22 mmol) in tetrahydrofuran (200 ml) was refluxed under nitrogen for 40 hours, then cooled. Water (1.0 ml), 15% aqueous sodium hydroxide (1.0 ml), and more water (3 ml) were added dropwise with vigorous stirring. The mixture was stirred for 30 minutes, then filtered. The filtrate was evaporated, leaving a pink oil. This was taken up in ethanol (20 ml), diluted with 50 ml ether, and concentrated nitric acid (1.3 ml) was added dropwise with vigorous stirring. A precipitate formed quickly, which was collected by filtration and washed with ether. Drying in vacuo provided Compound 4 as a white solid, mp 145-146° (2.5 g, 50%).

B. Preparation of Spermine Dialdehyde from Spermine bis-acetal

Spermine bis-acetal is dissolved in 1N HCl at a concentration of 100 mM (47.5 mg/ml). The solution is incubated in a 37° C. water bath for an hour. At the end of the incubation period, the 100 mM solution is diluted to 20 mM with purified water. The pH of the 20 mM solution is adjusted to between 5.0 and 6.5 using 10N NaOH. This PH adjusted 20 mM solution is the stock for all test material.

Preparation of Control Article

Control vehicle stock solution is obtained by titrating a 0.2M HCl solution with 10N NaOH and adjusting the pH to between 5.0 and 6.5. To obtain a control working solution, the stock solution is then diluted accordingly as with the test solution.

Material Used for Bioassays

The following materials were used in the Examples. Purified phytohemagglutinin (PHA-P) was obtained from Wellcome. Pokeweed mitogen (PWM) was obtained from Gibco. Tritated thymidine and chromium (51Cr) were obtained from New England Nuclear. Con A was obtained from Sigma. C57/B6, DBA/2, C3H and Balb/C mice were obtained from the Jackson Laboratory. Growth medium for human cell lines consisted of α-minimum essential medium (α-MEM) (Gibco) supplemented with penicillin (Gibco 50 Mg/ml), streptomycin (Gibco, 100 Mg/ml), L-glutamine (Gibco, 2.0 mM) and 2–10% calf serum (FCS, Gibco). The medium for the T cell proliferation assay was the same except RPMI 1640 (Gibco) was used instead of α-MEM; 10% FCS was used at all times.

C. Preparation of Mouse Bone Marrow and Spleen Cells

Mice were sacrificed by cervical dislocation and disinfected by dipping in a Dettol solution. Bone marrow cells were obtained from suitable long bones by flushing with a 0.25 gauge needle. Cells were then washed three times with RPMI before use.

Spleen cells were prepared by passing the spleen through a fine wire mesh. Cells were resuspended in RPMI and washed three times before use.

D. Preparation of Human B and T Lymphocytes and Lymphocyte Proliferation

Peripheral blood lymphocytes (PBL) were obtained from the blood of normal donors by using standard Ficoll-Hypaque gradient techniques. The T and non-T cells were separated by standard sheep red blood cell (SRBC) rosetting technique. Briefly, $5 \times 10^6$/ml PBL were incubated with 1% neuraminidase-treated SRBC, and rosetted cells were separated from non-rosetted cells on a Ficoll-Hypaque gradient. The rosetted cells were designated as T cells. Purified B lymphocytes were obtained from non-rosetted cells by removal of residual T cells using the Pan T monoclonal antibody OKT 11 and complement.

E. Human Lymphocyte Proliferation

T cell proliferation: $7 \times 10^4$–$10^5$ human T lymphocytes were cultured in flat bottom microtiter plates (Flow) in the presence of 0.1% PHA-P or 1/64 PWM for 4 days. 3H-thymidine (0.1 MCi/well) was added for the last 6 hours of the culture period. T cell dependent B cell proliferation: $4 \times 10^4$ T cells and $10^5$ B cells were cultured together in the presence of 1/64 dilution of PWM for 4 days. 3H-thymidine was added for the last 6 hours of the culture period. B cell proliferation was carried out in exactly the same manner with no T cells added to the culture. In all cases, cells were subsequently harvested onto filter paper using a multiple-channel automated cell harvester (Flow) and washed repeatedly with distilled water. Cell associated radioactivity was determined by scintillation counting in an automated counter. All of the results were expressed as % response calculated according to the formula:

$$\% \text{ response} = \frac{\text{cpm of supernatant-treated cultures}}{\text{cpm of control cultures}} \times 100$$

F. Mouse Lymphocyte Proliferation

Mouse spleen cells were cultured for 3 days in flat bottom microtiter plates at $10^5$ cells per well in the Presence of 2 mg/ml of Con A. 3H-thymidine (0.1 microcurie/well) was added for the last 4–6 hours of the culture period. Cells were harvested as described above.

G. Bone Marrow Transplantation in the Mouse Model

In bone marrow transplantation, bone marrow cells from normal donor mice were transplanted to totally histoincompatible and lethally irradiated recipients. All recipient mice received 9.5 Gy (950 rads) total body irradiation on day 0 and were then housed in microisolator cages thereafter. They were given autoclaved rodent laboratory chow throughout the whole study and also were allowed to feed ad libitum. Recipients also received 1.5 mg/kg of gentamicin subcutaneously for 20 days after irradiation. On the day of irradiation, bone marrow cells mixed in 3:1 ratio with spleen cells were removed from donors and incubated for an hour with different concentrations of spermine dialdehyde for 1 hour. Spleen cells were added to intensify subsequent graft vs. host disease (GVHD). After incubation, cells were washed 3 times and then injected intravenously into irradiated recipients. Signs of GVHD and survival were scored every day thereafter.

H. Graft Vs. Host Reaction in Rat (Popliteal Lymph Node Study) According to Method of Ford et al. Transplantation, Vol. 10, pp. 258–266 (1970).

Graft vs. host reaction in rats was measured by popliteal lymph node enlargement induced by reinjection of parental spleen cells into F1 recipients. (Lewis x BN) F1 rats were divided into groups of 10 and given daily IV injections of different doses of the test compound (spermine dialdehyde) or control preparation. Two days after the first injection, they received $9 \times 10^6$ spleen cells from the parental Lewis strain (0.3 ml of a $27 \times 10^6$ cells/ml preparation was injected under the skin of the ventral surface of each of the recipient's right hind foot). Injection of test compound and control article continued for 6 more days. On the seventh day, rats were sacrificed by $CO_2$ treatment. Both left and right popliteal lymph nodes were removed and cleaned of any adhering tissue. The extent of enlargement was measured by weighing both left and right lymph nodes and differences between the two were calculated.

I. Generation of Cytotoxic T Cell in Mice (In Vivo)

In vivo generation of cytotoxic T cells was performed according to the method described by Faanes et al., Clin. Exp. Immunol., Vol. 27, pp. 502–506 (1977). C57BL mice were arranged into groups of 10 and injected IP with different doses of spermine dialdehyde or control preparation. Two days after first injection, they received i.p. injection of $10^7$ DBA spleen cells which were prepared as described previously. Ten days after cell injection, C57 mice were sacrificed by cervical dislocation and cytotoxic T cells generated in the spleen were quantified by measuring the ability of those cells to lyse 51Cr labelled P815 target cells (a mastocytoma, cells DBA origin or Con A stimulated DBA spleen blasts). P815 cells or blasts were suspended at $10^7$ cells/ml and incubated with 200 MCi of 51Cr for 1 hour at 37° C. Cells were then washed 3 times and then mixed with C57BL spleen cells at ratios of 20:1, 10:1 and 5:1

(C57BL:P815) in a V-bottom microliter plate with a final volume of 200 ml. Cells were spun for 6 minutes and incubated for 4 hours at 37° C. After incubation, 100 Ml of supernatant was removed and counted in the gamma counter. The percentage of cytotoxic T cells was calculated:

$$\% \text{ total cytotoxicity} = \frac{{}^{51}Cr \text{ released by spleen cells } - \text{ spontaneous release}}{\text{Total release } - \text{ spontaneous release}} \times 100$$

J. Acute Toxicity

Two pairs of Swiss Webster mice were injected intraperitoneally at 200 mg and 400 mg/kg respectively and observed for toxic effects. Control groups were injected with control preparation. Two weeks after dosing, animals were necropsied and organs were examined for abnormalities.

K. Aldehyde Test

Aldehyde test was performed according to the method described by Sawicki et al., Analytical Chem., 33, 93-96 (1961). Briefly, 50 Ml of 0.4% solution of 50 Ml of the test solution. The mixture was allowed to stand at room temperature for 30 minutes, then 200 Ml of a 0.2% solution of ferric chloride was added and the mixture was then left at room temperature for 10 minutes. Six hundred and fifty Ml of acetone was then added to the sample with slow agitation and the color intensity of the sample was quantitated by spectrophotometric reading at wavelength 670 nanometers.

L. Skin Graft Transplantation

In a skin graft transplant experiment, Balb/c ($H2^d$) skin grafts were transplanted onto C3H mice according to the procedure described in 1. Spermine dialdehyde was administered s.c. right after transplantation and continued throughout the study. Cyclosporin A (CsA) was run along as a positive control.

M. Delayed Type Hypersensitivity

Delayed type hypersensitivity was induced in the footpad of B6D2F1 mice by using sheep red blood cells (SRBC) as the antigen. Briefly, 0.2 ml of 0.01% SRBC was injected i.v. into B6D2F1 mice. Four days later, they were challenged in the footpad with 50 $\mu$l of 20% SRBC. Swelling of the footpad was measured 24, 48, and 72 hours later. Spermine dialdehyde was administered i.p. initiating from the day before immunization. After challenge in the footpad, B6D2F1 mice were given an intramuscular (i.m.) injection beside the challenge site one hour after challenge. Some mice received no i.p. administration and were only given one i.m. injection after the challenge. Results are shown in FIG. 7.

II. RESULTS

A. Effect of Spermine Dialdehyde on Human T and B Lymphocytes

Human lymphocytes were prepared and separated into T and B lymphocytes as described previously. T and B lymphocytes were incubated with different concentrations of spermine dialdehyde for 1 hour at 37° C. Cells were washed 3 times with RPMI and were then set up in a PHA driven T cell proliferation assay or pokeweed mitogen (PWM) driven B cell proliferation assay. Results are illustrated in FIG. 1. As can be seen, spermine dialdehyde inhibited T cell proliferation by 85% at $0.62 \times 10^{-2}$ mM whereas a much greater quantity was required to suppress B lymphocyte proliferation. Thus, spermine dialdehyde preferentially suppresses T cell proliferation with a much less suppressive effect of B lymphocytes. Furthermore, these data suggest that spermine dialdehyde could irreversibly inactivate T lymphocytes after a brief incubation of 1 hour (5-10 minute incubation was in fact sufficient—data not shown). This novel property distinguishes spermine dialdehyde from other immunosuppressive molecules such as cyclosporine A or prednisone which are all reversible in nature.

B. Effect of Spermine Dialdehyde on Mouse Spleen and Bone Marrow Cells

Figure 2:
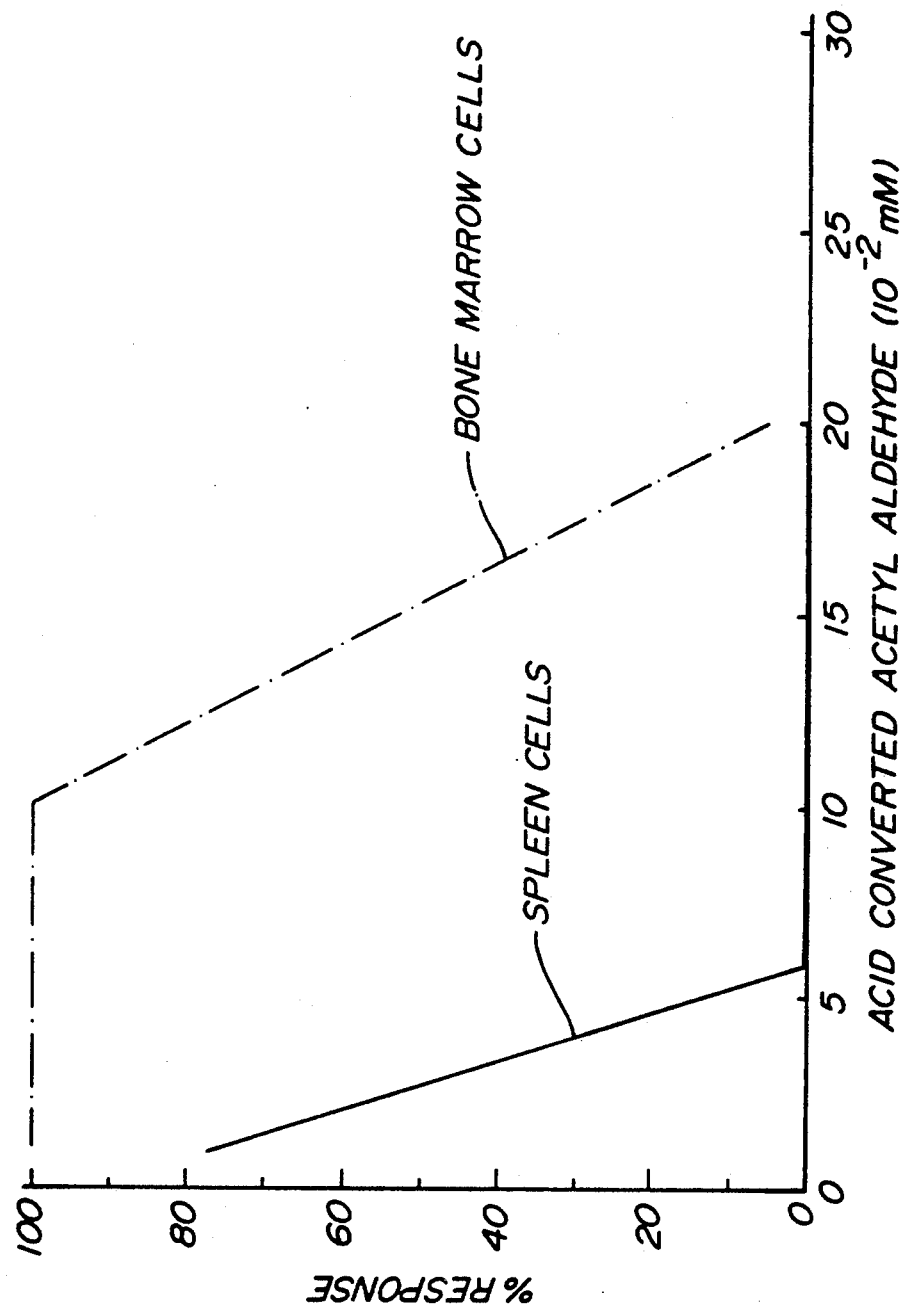
FIG. 2 demonstrates in vitro suppression mediated by spermine dialdehyde. Mouse spleen and bone marrow cells were incubated separately with different concentrations of spermine dialdehyde in vitro for 1 hour. Cells were washed extensively and set up in a Con A stimulated proliferation assay. A graph is depicted wherein percentage response (spleen cells indicated by an unbroken line; bone marrow cells indicated by a broken line) is plotted as a function of various concentrations of acid converted acetyl aldehyde ($10^{-2}$ mM).

Mouse bone marrow and spleen cells were each incubated for 1 hour with different concentrations of spermine dialdehyde. Cells were then washed 3 times with RPMI and set up in a Con A driven proliferation assay. Results are depicted in FIG. 2. Spleen cells, as can be seen, were much more susceptible to suppression mediated by spermine dialdehyde than bone marrow cells.

Figure 3:
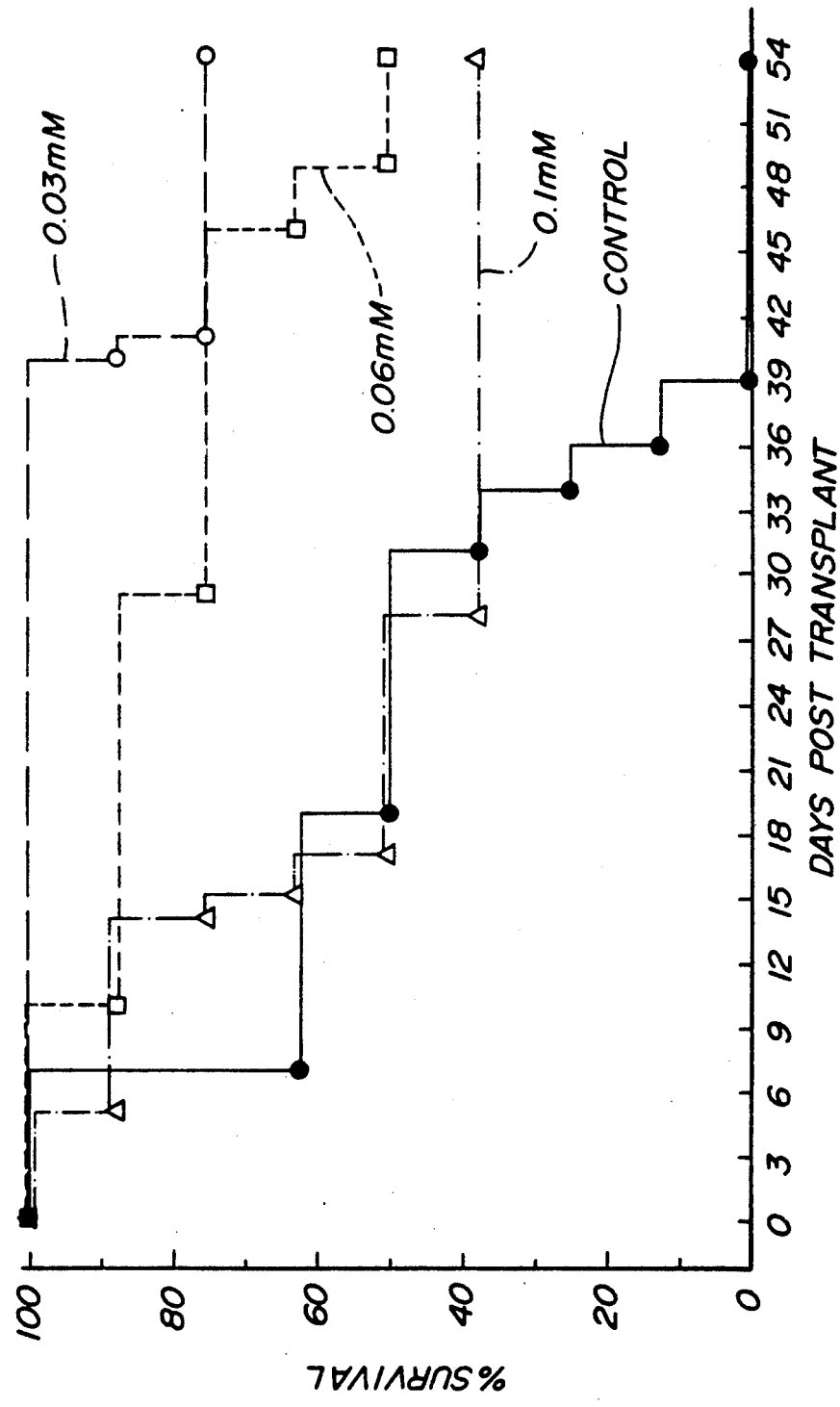
FIG. 3 indicates the effect of spermine dialdehyde on survival after allogenic BMT in mice (C57BL/6-AKR). C57BL spleen and bone marrow cell mixtures were treated with different concentrations of spermine dialdehyde or control preparation and injected i.v. into lethally irradiated AKR mice. A graph is depicted wherein percentage survival is scored as a function of days post transplant. Dosage 0.03 mM is indicated by a broken line interrupted by clear circles; dosage 0.06 mM is indicated by a broken line interrupted by squares; dosage 0.1 mM is indicated by a broken line interrupted by triangles; and the control is indicated by a broken line interrupted by black circles.

C. Ex Vivo Treatment of Bone Marrow Graft With Spermine Dialdehyde Alleviated Graft Vs. Host Disease in Recipients and Prolonged Survival Time Bone marrow and spleen cell mixtures (3:1 ratio) from C57BL mice were incubated with control preparation or various concentrations of spermine dialdehyde for 1 hour. Cells were then washed extensively and injected intravenously into lethally irradiated histoincompatible AKR mice. Signs of graft vs. host diseases such as hunched back, diarrhea, alopecia, and physical conditions were recorded daily. Survival times of reconstituted mice are shown in FIG. 3. Control mice showed severe signs of acute GVHD initiating around 10 days after transplantation. Mice receiving bone marrow treated with spermine dialdehyde manifested only mild signs of GVHD. The very high dose groups of 0.2 mM exhibited marrow toxicity and animals died around the same time as the irradiated controls probably due to lack of reconstitution. Mice receiving marrow treated with lower doses of spermine dialdehyde (0.03-0.06) showed significantly prolonged survival time. Thus treatment with lower doses of spermine dialdehyde inactivated T lymphocytes without being toxic to marrow cells and allowed animals to reconstitute with little sign of GVHD. These data suggest that spermine dialdehyde could be employed to treat human bone marrow samples ex vivo before bone marrow transplantation to alleviate subsequent GVHD which is usually lethal to the patients.

Figure 4:
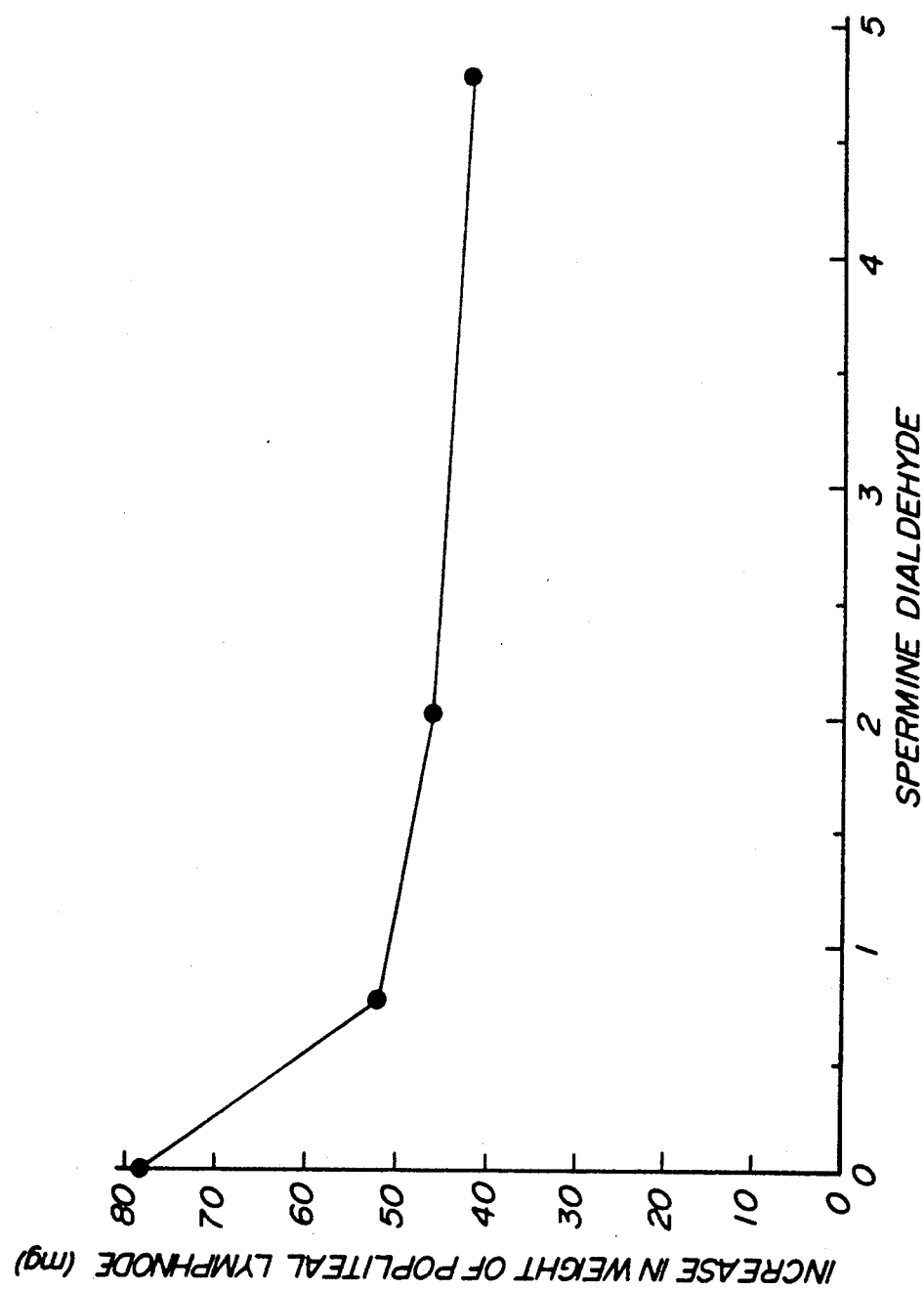
FIG. 4 indicates the effect of spermine dialdehyde on graft vs. host reaction as illustrated by a popliteal lymph node assay. (LewXBN) rats were injected i.v. daily for 8 days with different doses of spermine dialdehyde. On day 2, BN rat spleen cells were injected subcutaneously into the left foot pads of the (LewxBN)$F_1$ rats. These rats were sacrificed in 7 days and weights of both left and right popliteal lymph nodes were removed. The increase in weight of popliteal lymphocytes mg) is plotted as a function of spermine dialdehyde concentrations ($10^{-2}$ mM) used.

D. Suppression of Graft Vs. Host Reaction in Rats by In Vivo Injection of Spermine Dialdehyde Graft vs. host reaction was generated in the form of popliteal lymph node in F1 recipients by subcutaneous injection of parental spleen cells. Spermine dialdehyde was administered intravenously starting 2 days before parental spleen cell injection and continued until the day of lymph node measurement. Increase in popliteal lymph node swelling was scored by difference in weight between test (left) and control (right) lymph node. Results were shown in FIG. 4. Substantial swelling was observed in test lymph nodes. Intravenous injection of spermine dialdehyde significantly suppressed the GVH reaction as depicted by diminutive popliteal lymph node swelling. This GVH reaction is a typical manifestation of MHC class II reaction involving allogenic T lymphocytes. Spermine dialdehyde, when given intravenously suppressed this reaction, suggesting that this molecule mediates the same effect in vivo as in vitro, that is, it acts as a potent suppressor of T cell reactivity.

Figure 5:
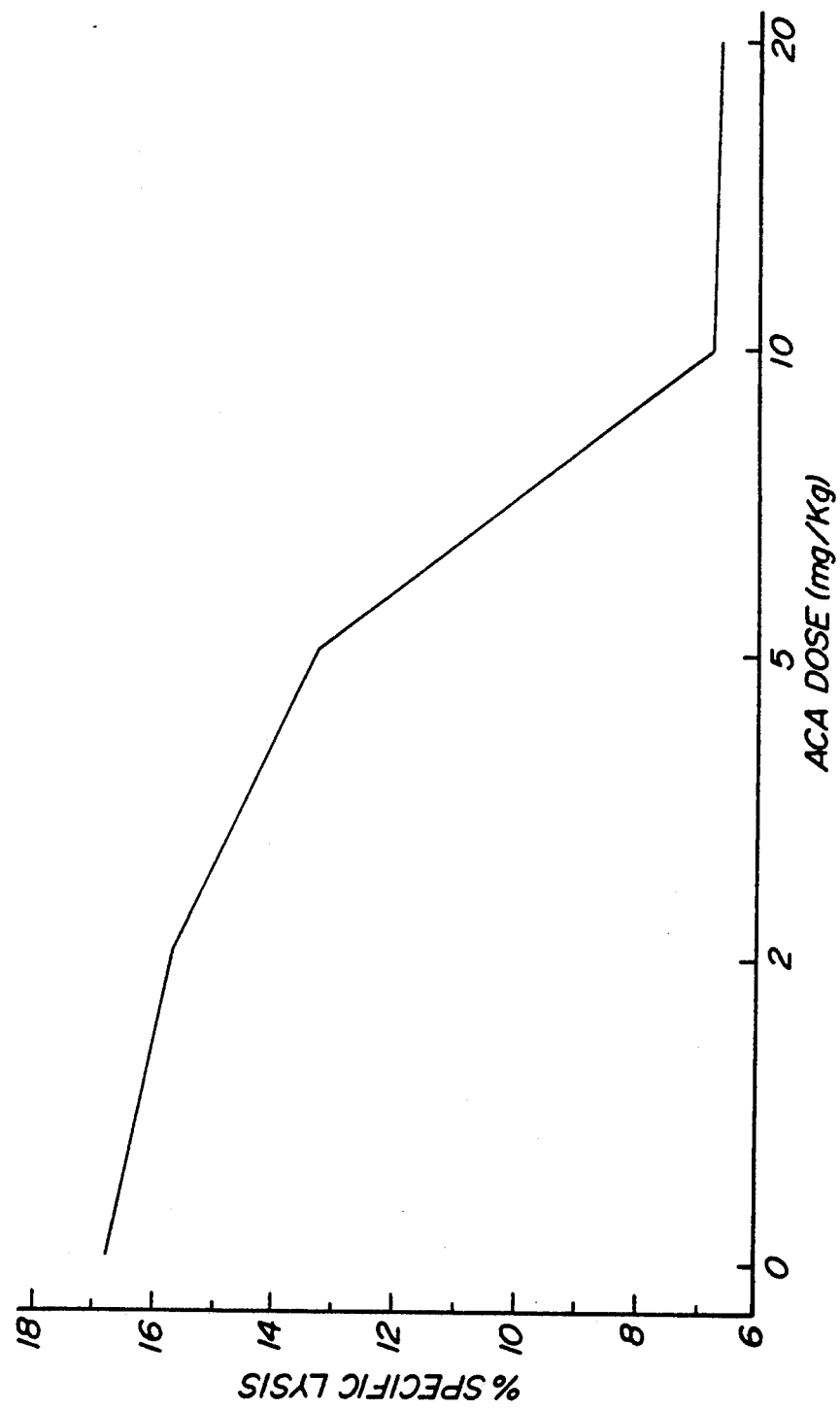
FIG. 5 indicates the in vivo effect of spermine dialdehyde on cell mediated lympholysis in mice. C57BL mice were injected i.p. daily with different doses of spermine dialdehyde. On day 2, they also received $10^7$ DBA spleen cells. Seven days later, animals were sacrificed and percentage of cytotoxic T cells (measured by % specific lysis generated in the spleen was calculated and plotted as a function of concentration of spermine dialdehyde ACA dose (mg/kg).

E. In Vivo Suppression of Generation of Mouse Cytotoxic T Cells by Spermine Dialdehyde About 10 days after receiving DBA spleen cells, C57BL mice will generate cytotoxic T cells in their spleens which lyse P815 mastocytoma cells bearing DBA specific antigens Since cytotoxic T cells play an important role in the mediation of organ graft rejection, in vivo suppression of cytotoxic T cell generation may lead to prolonged graft survival. Spermine dialdehyde, when administered i.p., suppressed the generation of cytotoxic T cells in a dose related manner (FIG. 5). Dose of 10 mg/kg i.p. appeared to attain maximum suppression which corresponds well with the dose required to achieve maximum suppression of GVH reaction in vivo (5 mg/kg i.v., FIG. 4).

The two models described above demonstrated for the first time that synthetic spermine dialdehyde is effective as an immunosuppressive compound in vivo.

F. Acute Toxicology Results

Two pairs of Swiss Webster mice were injected intraperitoneally at 200 mg and 400 mg/kg for toxic effects. Spermine dialdehyde appeared to be acutely irritating in these test animals as indicated by squinting and writhing. Mice receiving 200 mg/kg exhibited no other toxic effect whereas those injected with 400 mg/kg showed abdominal or whole body edema for five days. At necropsy 14 days after injection, only the 400 mg/kg group showed any positive findings which consisted of a mildly distended abdomen and scab formation at the injection site. This data differed significantly from results reported by Israel et al Supra which showed that the LD100 of this molecule is 40 mg/kg.

G. Prolongation of Skin Graft Survival

Figure 6:
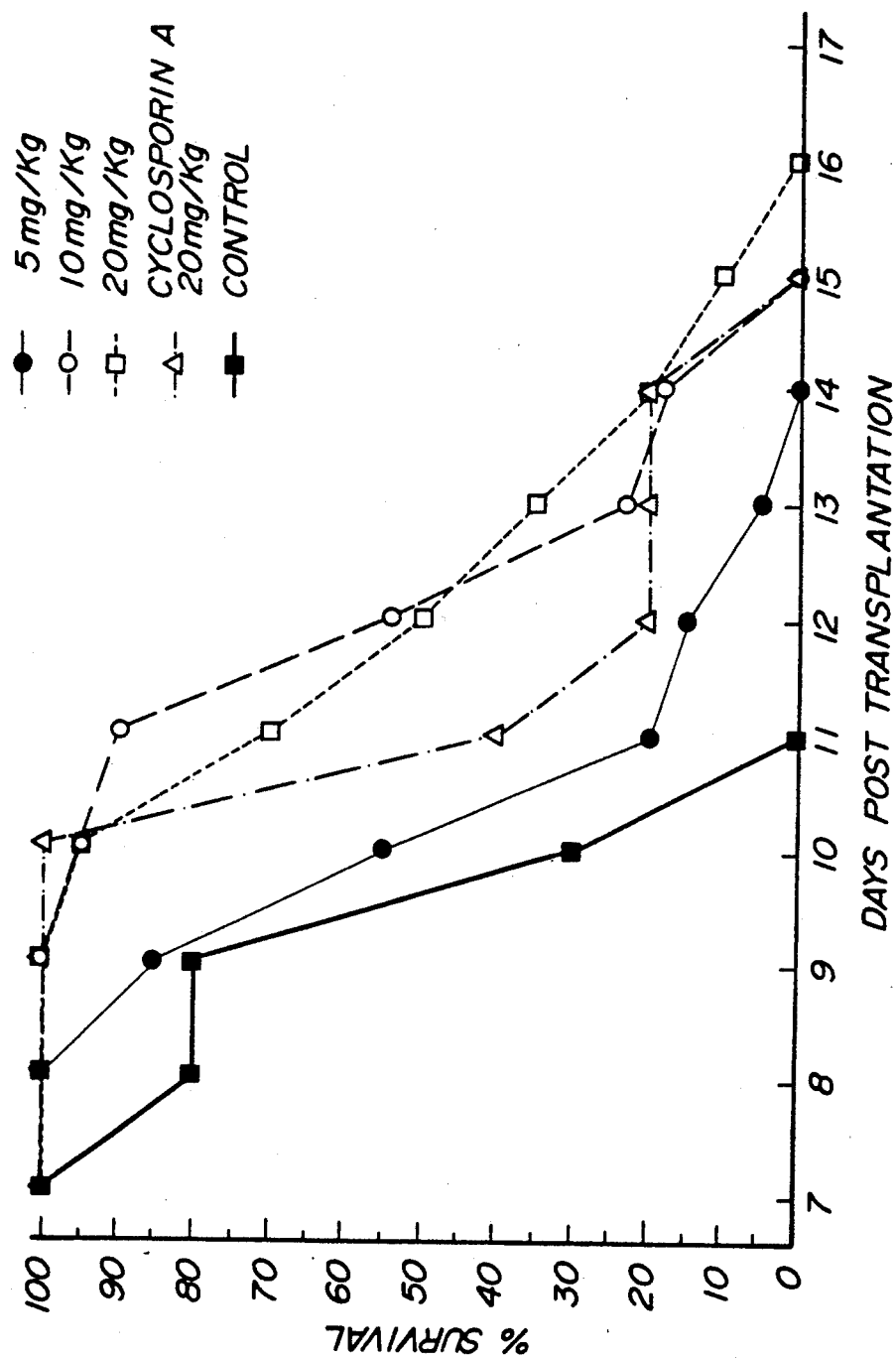
FIG. 6 indicates prolongation of skin graft survival by spermine dialdehyde. In a skin graft transplant experiment, Balb/C (H2$^d$) skin grafts were transplanted into C3H mice. Spermine dialdehyde was administered S.C. right after transplantation, and continued throughout the study. Cyclosporin A was run as a positive control. % skin graft survival was plotted versus days post transplantation. Dosage 5 mg/kg was indicated by a broken line interrupted by a black circle; 10 mg/kg by a broken line interrupted by a clear circle; 20 mg/kg by a broken line interrupted by a clear square; cyclosporin A 20 mg/kg by a broken line interrupted by a triangle; and control by a broken line interrupted by a black square.

As depicted in FIG. 6, CsA and all 3 doses of spermine dialdehyde prolonged skin graft survival, especially 10 mg/kg and 20 mg/kg of spermine dialdehyde.

H. Suppression of Delayed Type Hypersensitivity

B6D2F1 mice receiving both i.p. administrations and one injection in the footpad showed significant reduction in swelling when measured 24 hours after challenge and also 48 hours later. Mice receiving 1 injection in the footpad did not exhibit reduction in swelling 24 hours later, but did so 48 hours later.

Results suggest that mice receiving spermine dialdehyde both systemically and locally showed reduced swelling measured at 24 or 48 hours after challenge. Mice receiving spermine dialdehyde only after challenge showed swelling similar to that of mice receiving control vehicles 24 hours later. However, 48 hours later, reduced swelling compared to that of the control group was observed.

Delayed type hypersensitivity is a T-cell mediated immune response. After immunization with the antigen, mice would be sensitized with specific T cells responding to the antigen. These T cells will migrate to various parts of the body including the footpad. During challenge with the same antigen, these T cells will be reactivated and result in the release of lymphokines, some of which will be chemotactic for monocytes, macrophages and neutrophils. Accumulation of these cells then leads to a local inflammatory response causing substantial swelling. When spermine dialdehyde was administered i.p. before and right after sensitization, it probably suppressed T cell responses to the antigen and after challenge the injection at the footpad suppressed T cells and other cells involved in inflammation (reduction of swelling was not significant if the footpad injection was omitted). However, if injection was given only after challenge in the footpad, suppression of inflammatory response could also be observed 48 hours later. These findings suggest that spermine dialdehyde suppressed T cell response to the antigen both at the sensitization and inflammatory stages. Suppression, however, was most significant when spermine dialdehyde was administered before and during sensitization and also after challenge. Combined injections suppressed both the generation of sensitized T cells and the de novo inflammatory response.

What is claimed is:

1. A method for the selective immunosuppression of living cells which comprises administering to said cells, in substantially pure form, a compound having the formula:

in an amount, and for a period of time suitable to induce a decrease in the proliferation of a T cell subpopulation present among said living cells.

2. The method of claim 1 wherein said compound is 95%-97% pure, as measured by mass spectroanalysis.

3. The method of claim 2 wherein said compound is synthesized de novo, using organic synthesis techniques.

4. The method of claim 3 wherein said compound is administered to living cells in a suitable physiologically compatible vehicle.

5. The method of claim 4 wherein said selective immunosuppression is substantially irreversible.

6. The method of claim 4 wherein said living cells are selected from the group consisting essentially of bone marrow cells, spleen cells, peripheral lymphocytes, and any combination thereof.

7. The method of claim 6 further comprising the step of administering said immunosuppressed cells to a living organism.

8. The method of claim 7 wherein said administration is an intravenous injection.

9. The method of claim 7 wherein said administration is a bone marrow transplant.

10. The method of claim 4 wherein said selective immunosuppression is a decrease in the proliferation of a cytotoxic T cell subpopulation.

11. A therapeutic method for suppressing an immunological graft tissue vs. host reaction in an individual for whom said therapy is indicated, comprising administration to said individual, in substantially pure form, and in an amount and for a period of time effective to suppress said reaction, a compound having the formula:

12. The method of claim 11 wherein said administration is intravenous.

13. The method of claim 12 wherein said amount is about 5 mg/Kg.

14. An ex vivo method of treatment of bone marrow extracts from a living organism to suppress proliferation of a T cell population in said extract, which comprises the administration to said extract in substantially pure form and in an amount and for a period of time sufficient to suppress T cell proliferation, a compound having the formula:

15. The method of treatment of claim 14 wherein said compound is about 95% to about 99% pure as measured by mass spectroanalysis.

16. The method of treatment of claim 15 wherein said compound is synthesized de novo, using organic synthesis techniques.

17. The method of treatment of claim 16 wherein said compound is administered to the cells in a suitable physiologically compatible vehicle.

18. A therapeutic method for suppression of an immunological graft tissue vs. host reaction in an individual for whom said therapy is indicated, comprising the steps of:

a) obtaining from said individual, living cells selected from the group consisting essentially of bone marrow cells, spleen cells, peripheral lymphocytes, or any combination thereof;

b) administering to said living cells so obtained, in substantially pure form and in an amount and over a period of time sufficient to suppress T cell proliferation, a compound having the formula:

c) administering said living cells of step b) so treated to said individual.

19. The method of claim 18 wherein said living cells of a) are selected from the group consisting essentially of bone marrow cells and spleen cells, or a combination thereof.

20. The method of claim 19 wherein said administration of step c) is intravenous.

21. The method of claim 20 wherein said living cells for said administration are a combination of spleen cells and bone marrow cells.

22. The method of claim 19 wherein said living cells of step a) are bone marrow cells.

23. The method of claim 22 wherein said amount sufficient to suppress T cell proliferation of step b) is about 0.03 mM–0.06 mM.

24. The method of claim 23 wherein said administration of step c) is a bone marrow transplant.

25. The method of claim 23 wherein said administration of step c) is intravenous.

* * * * *